United States Patent [19]

Alley, III

[11] 4,023,121
[45] May 10, 1977

[54] OSCILLATOR FOR DEMAND HEART PACER

[75] Inventor: Lawrence Everett Alley, III, North Easton, Mass.

[73] Assignee: ARCO Medical Products Company, Leechburg, Pa.

[22] Filed: Sept. 16, 1975

[21] Appl. No.: 613,819

Related U.S. Application Data

[63] Continuation of Ser. No. 430,827, Jan. 4, 1974, Pat. No. 3,926,197.

[52] U.S. Cl. .................. 331/111; 128/419 PG; 307/279; 307/304; 331/173
[51] Int. Cl.² ............... H03K 3/353; A61N 1/36
[58] Field of Search .................. 331/111, 113 R; 128/419 P, 419 PG, 419 PT; 307/304, 279

[56] References Cited

UNITED STATES PATENTS 3,562,559  2/1971  Rapp .................. 331/113 R X
3,768,486  10/1973  Berkovits et al. .......... 128/419 PG Primary Examiner—Siegfried H. Grimm
Attorney, Agent, or Firm—Richard A. Bachand

[57] ABSTRACT

A demand heart pacer which includes an oscillator, an amplifier for receiving and amplifying naturally occurring heart pulses, a monostable multivibrator activated by amplified naturally occurring heart pulses to generate a disabling pulse, and means for disabling the oscillator upon occurrence of a disabling pulse is of complimentary metal oxide semiconductor devices to present a capability of operating with low power dissipation to facilitate implantable heart pacer use having an enhanced power supply lifetime. The heart pacer produces stimulation pulses in an "inhibit mode" at a first frequency and stimulation pulses in a "fixed rate mode" at a second frequency, the difference in the first and second frequencies being indicative of the power supply voltage to provide a monitor of its state or condition. The heart pacer additionally employs an oscillator inhibitor, which includes a field effect transistor biased to a level which is increased upon reception of high frequency noise, to prevent conduction, and which additionally operates to define a variable second half of a refractory period to distinguish noise at a frequency approximately twice that of an acceptable heartbeat frequency.

6 Claims, 6 Drawing Figures

OSCILLATOR FOR DEMAND HEART PACER

This is a continuation of application Ser. No. 430,827, filed Jan. 4, 1974, now U.S. Pat. No. 3,926,197.

BACKGROUND OF THE INVENTION

1. Field of the Invention

This invention relates to improvements in heart pacer circuits, and in oscillators for use therein, and, more particularly, to improvements in heart pacer circuits of the type which supply stimulation pulses in the absence of naturally occurring heart pulses. 2. Description of the Prior Art In the production of heart pacers, devices which produce electrical pulses for application to a heart to stimulate its beat, much emphasis has been recently placed upon achieving a heart pacer of relatively small size to facilitate its implantation into the body of the user. This has resulted in increased emphasis upon achieving circuitry of high reliability and quality, since once the heart pacer device is implanted, repairs although mechanically simple, may involve surgical operations just to achieve access to the device.

The heart pacers commonly used are of three general classifications, fixed rate, synchronous, and demand pacers. The fixed rate pacer produces stimulation pulses at a particular fixed rate, such as 72 beats per minute, at its own internally controlled rate, regardless of the occurrence of natural heart pulses. Synchronous heart pacers, on the other hand, produce stimulation pulses in synchronism with a particular natural heart pulse, such as a predetermined time after the production of a heart P wave. Demand heart pacers produce heart stimulation pulses only in the absence of a particular heart pulse. Typically, the demand heart pacers are activated by the absence of a naturally occurring R wave, since the R wave is the largest heart produced wave, and easiest to detect. Thus, after a demand heart pacer has been installed, if the wearer's heart fails to produce an R wave, which would have caused the heart muscle to naturally contract, the demand pacer produces an artificial pulse which is applied to the heart via a conductive lead physically attached to the heart to induce the desired heart beat or contraction.

Ordinarily, demamd heart pacers are operated in the so-called "inhibit" mode, the output pulse generated by the demand heart pacer being inhibited by the heart producing its own naturally occurring heart pulse, although demand heart pacers are usually operable in a "fixed rate" mode under certain conditions. For example, typically demand heart pacers have a built in switch activatable from outside the user's body, such as by exposure to a magnetic field, or the like, to cause the heart pacer to switch from its "inhibit" mode to the "fixed rate" mode. Also, other naturally occurring conditions typically cause the demand heart pacer to switch to a fixed rate mode, such as signals or noise received at an undesirable frequency, which interfere with the pacer's detection of the naturally occurring heart pulses.

Because heart pacers are typically implanted, they ordinarily have as an integral part a power supply of one or more batteries to power the electronics to produce the heart stimulation pulses. Ordinarily, one or more chemical batteries are used; however, because of the relatively short useful lifetimes of chemical batteries, nuclear batteries have been recently considered for power supply sources, to increase the useful lifetime of the heart pacer.

One of the requirements, therefore, evident in the circuitry for use in conjunction with either chemical or nuclear batteries, is that the circuitry have power dissipation as low as possible. Furthermore, because nuclear batteries operate at relatively low voltages, the particular circuitry used with such batteries must be operable at such low voltages, and draw relatively low current, as well.

This introduces a particularly crucial design consideration in the heart pacer circuitry, that of having a quiescent state between heart pulses detected or produced which draws the minimum possible amount of current. For example, it has been proposed that in such quiescent state, as many as possible of the operable devices, such as transistors, or the like, be biased into nonconduction so as not to dissipate any power, while not actually producing stimulation pulses.

Another difficulty resulting from the pacer being implanted is in determining the state or condition of the power supply. For example, after the pacer has been implanted for an extended time, there has been no way of directly determining the condition of the power source, other than by monitoring the pulse production rate. Typically, the pulse production rate of the fixed rate oscillator of the pacer is designed to exhibit a lower pulse production rate at lower power supply voltages. However, this method is susceptable to inaccurate indications since components within the pacer circuit particularly the timing resistors and capacitors of the multivibrator circuit, may exhibit changes in their electrical values with age, such component value drifts producing increased or decreased heart production frequencies, resulting in possible erroneous indications of the battery condition.

Additionally, one of the problems presented in the prior art heart pacers is that the heart stimulation pulse decreases in power as the battery voltage decreases. Typically, the duration of the heart stimulation pulse produced is maintained at a constant level, therefore, the electrical power within the heart stimulation pulse envelope decreases as the battery voltage decreases. This is undesireable since it may necessitate replacement of the pacer at a time when pulses are being produced timely, but of power insufficient to stimulate heart contractions.

In addition to the power requirements, heart pacers must be unaffected by noise both from outside sources, and from the heart itself. For example, the heart pacer must be capable of distinguishing high frequency noise generated, for instance, by a nearby automobile ignition, from the electrical pulses of interest naturally occurring or generated within the heart in order that the pacer is not inhibited erroneously under the influence of the undesireable noise. The heart itself generates undesireable noise, which, although inconsequential to the heart organ, is undesireable for detection by the pacer. This heart noise, therefore must be distinguished, particularly after each heart beat stimulated by the pacer or naturally occurring. To distinguish this noise, typically, heart pacers have elements to time a "refractory period" built into their circuitry to block the detection of undesireable heart pulses occurring within that period. One of the difficulties encountered, however, is that in most commercially available pacers, if a noise signal is impressed upon the pacer at a frequency approximately twice that of a natural heart beat, just beyond the termination of a refractory period (i.e., one noise pulse falling within the refractory period, a subsequent pulse falling just outside the refractory period), the heart pacer will detect the second heart pulse and interpret it as a naturally occurring heart pulse, causing the stimulation pulse to be inhibited, whether it should be or not.

SUMMARY OF THE INVENTION

In light of the above, it is, therefore, an object of the invention to present a heart pacer which produces pulses in the absence of naturally occurring heart pulses for application to a heart for stimulation thereof.

It is another object of the invention to present a heart pacer which operates at lower voltage and current levels than heart pacers heretofore advanced.

It is another object of the invention to present a heart pacer which produces an indication of the power supply voltage, independently of changes in component values.

It is still another object of the invention to present a heart pacer in which the pulse width is relatively constant over a wide operating voltage range.

It is another object of the invention to present a heart pacer in which the heart stimulating pulse has approximately the same stimulation power over a range of supply voltages.

It is still another object of the invention to present a heart pacer which provides means for inhibit mode and fixed rate mode frequencies which are comparable to indicate the power supply voltage.

It is still another object of the invention to present a heart pacer which produces heart stimulation pulses at a first frequency in an "inhibit" mode, and stimulation pulses at a second frequency in a "fixed rate" mode, the first and second frequencies being comparable to produce a calculatable difference indicative of the power supply voltage.

It is still another object of the invention to present a heart pacer circuit which employs principally CMOS devices.

These and other objects, features, and advantages will become apparent to those skilled in the art from the following detailed description, when read in conjunction with the appended claims and accompanying drawing.

In the broad aspect, the invention presents for use in a heart pacer a circuit employing complimentary metal oxide semiconductor devices to control the charging and discharging of a timing capacitor. The heart pacer circuit is of the type utilizing a timing capacitor to control the oscillation rate of an oscillator which generates pulses applied to and amplified by an output stage for transmission and application to the heart to be stimulated. The heart pacer, in another aspect of the invention includes an amplifier having an input connectable to the heart for receiving and amplifying naturally occurring heart pulses. A monostable multivibrator is activated by an amplified naturally occurring heart pulse to generate a disabling pulse. Means are provided to which the disabling pulse is applied to produce the discharge of the timing capacitor, and in this heart pacer embodiment, the amplifier, monostable multivibrator, and discharging means employ field effect transistors. Thus, in its broad aspect, a transistorized circuit is presented generating electrical heart stimulating pulses in which complementary metal oxide semiconductor devices are used for the transistor components thereof.

In another aspect of the invention, a heart pacer is presented for producing heart stimulation pulses in the absence of naturally occurring heart pulses. The pacer includes means connectable to the heart for generating stimulation pulses at a heart beat rate the stimulation pulse generating means is connected to means for discharging the timing capacitor for inhibiting selected stimulation pulses. Means for producing a wave form from the generated inhibiting pulse for activating the capacitor discharge means is interconnected between the inhibiting pulse generating means and the stimulation pulse generating means. Means includes at least one field effect transistor biased normally below a threshold voltage to a normally nonconducting state and biased above the threshold voltage to a conducting state by at least a portion of the wave form.

In still another aspect of the invention, a heart pacer of the type energized by a voltage source is presented, which includes an oscillator for producing pulses at a rate for application to the heart. Means for controlling the frequency of production of pulses of the oscillator includes therewithin a field effect transistor means having a threshold voltage for conduction for operating the controlling means. Means for producing a wave form derived from a single natural heart pulse, the wave form produced having a portion beyond the threshold voltage of the field effect transistor, is operably connected to the controlling means. The magnitude of the portion of the wave form beyond the threshold voltage is relatable to the voltage of the voltage source whereby the frequency of the oscillator varies with the voltage of the voltage source.

In still another aspect of the invention, a heart pacer is presented of the type having an oscillator, and means for controlling the oscillation frequency at a first fixed rate. Means are provided in the heart pacer for providing a threshold voltage to a field effect transistor in an inhibit mode for pacing at a second rate different from the first rate by an amount relatable to the supply voltage.

BRIEF DESCRIPTION OF THE DRAWINGS

The invention is illustrated in the accompanying drawing, wherein.

DESCRIPTION OF THE PREFERRED EMBODIMENTS

In achieving one of the principal objects of the invention, the heartpacer circuit, in accordance with the invention, utilizes or employs field effect transistors (FET's), and, more particularly, FET's of the type commonly referred to in the art as metal oxide semiconductors (MOS), and, still more particularly, of the MOS type transistors employed in complimentary pairs, referred to as complimentary metal oxide semiconductors (CMOS), including ordinarily a p-channel device and an n-channel device connected in a complementary fashion.

It has been found that through the use of such CMOS and FET devices, a heartpacer circuit can be achieved which requires considerably less current and voltage from the particular voltage source employed with the circuit. Conversely, through the use of CMOS and FET devices, a heart pacer circuit can be operated with power sources much smaller than conventional transistorized circuits.

Toward achieving the object of fabricating a circuit for use, for example, with a nuclear battery for implantation into a human, it is desirable that the circuit and battery implanted be capable of functioning or operating over extended periods of time, for instance, on the order of 10 or 15 years, or more. Thus, the power requirements of the electronics of the circuit are particularly significant in the circuit design to present minimum power drain upon the power source to realize as long as useful operable lifetime as possible. It has been discovered that the particular characteristics of CMOS and FET devices are particularly suitable to achieve such low power requirements, and are particularly suitable for use in heartpacer circuitry.

Figure 1:
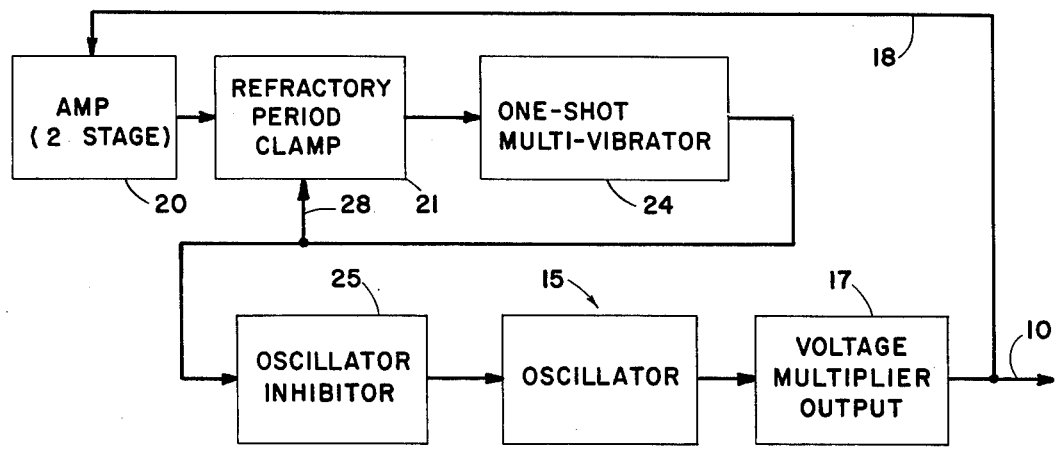
FIG. 1 is a box diagram of the general functional parts of the heart pacer, in accordance with the principles of the invention, illustrating their functional interconnections.

The general box diagram of the demand heartpacer, presented in accordance with the invention, shown in FIG. 1, includes a heart lead 10 which is connectable to the heart. Such heart leads are well known in the art structurally and with respect to the required insertion techniques, and are not described further herein in detail.

The basic portion of the circuit is the oscillator portion, denoted generally by the reference numeral 15. The oscillator 15 generally functions to provide heart stimulation pulses at the desired stimulation rate, for example, 72 pulses per minute. The pulses from the oscillator are applied to a voltage multiplier output 17 the output of which is connected to the heart lead 10 for application to the heart. Thus, the basic oscillator circuit 15 and voltage multiplier output 17 supply heart stimulation pulses at the desired rate, and, if desired, can be utilized without additional circuitry in this manner, to constitute a socalled fixed rate heartpacer; i.e., a heartpacer which, regardless of the needs of the heart, supplies heart pulses at the particular rate or frequency to which the oscillator is tuned or adjusted.

In many instances, however, it is desirable to supply stimulation pulses to the heart only if the heart fails or is unable to supply its own pulses. Thus, in a so-called demand pacer the naturally occurring electrical heart pulses are detected. If the naturally occurring heart pulses for a particular heartbeat are present, the heartbeat which normally would be supplied by the oscillator 15 is inhibited or cancelled, and a timing period initiated corresponding to the natural period between heartbeats. If subsequently the heart fails to beat or produce its own heart stimulation pulse, the oscillator will not be inhibited, and an artificial pulse will be produced and applied to the heart lead 10.

To effect such demand capabilities, a connection 18 is made to the heart lead 10 to conduct electrical pulses exhibited on the lead 10 to an amplifier 20. The pulses within the amplifier 20 are amplified and applied to a refractory period clamp 21. The purpose of the refractory period clamp is to reject any signals from the amplifier 20 during a period known as the "refractory period" of, for example, 125 milli-seconds. Physiologically, the heart, after an artificial heart pulse has been applied, commonly reacts to the stimulation pulse by producing spurious electrical signals which can be conducted by the heart lead 10 and detected within the amplifier 20. Without some means for blocking such spurious heart pulses, the circuitry of a heartpacer may be "tricked" into receiving a heart pulse, thereby delaying the subsequent pulse produced to be applied to the heart. Thus, the refractory period clamp 21 functions to block any pulses from the amplifier 20 during the 125 milli-second period immediately following the reception of a naturally occurring heart pulse (or, as will become apparent below, after the reception of a stimulation pulse from the pacer).

The heart pulse received and amplified by the amplifier stage 20 is then directed to a one-shot multivibrator 24. The one-shot multivibrator, upon reception of such heart pulse produces an output pulse which is directed to an oscillator inhibitor 25, and, concurrently, fed back by a line 28 to the refractory period clamp 21. The oscillator inhibitor 25, upon reception of the pulse from the one-shot multivibrator disables or inhibits the oscillator 15 for one pulse period, for example, by discharging a timing capacitor within the oscillator. By virtue of the feedback line 28 the refractory period clamp 21 is activated for the predefined refractory period from the one-shot multivibrator 24.

Figure 2:
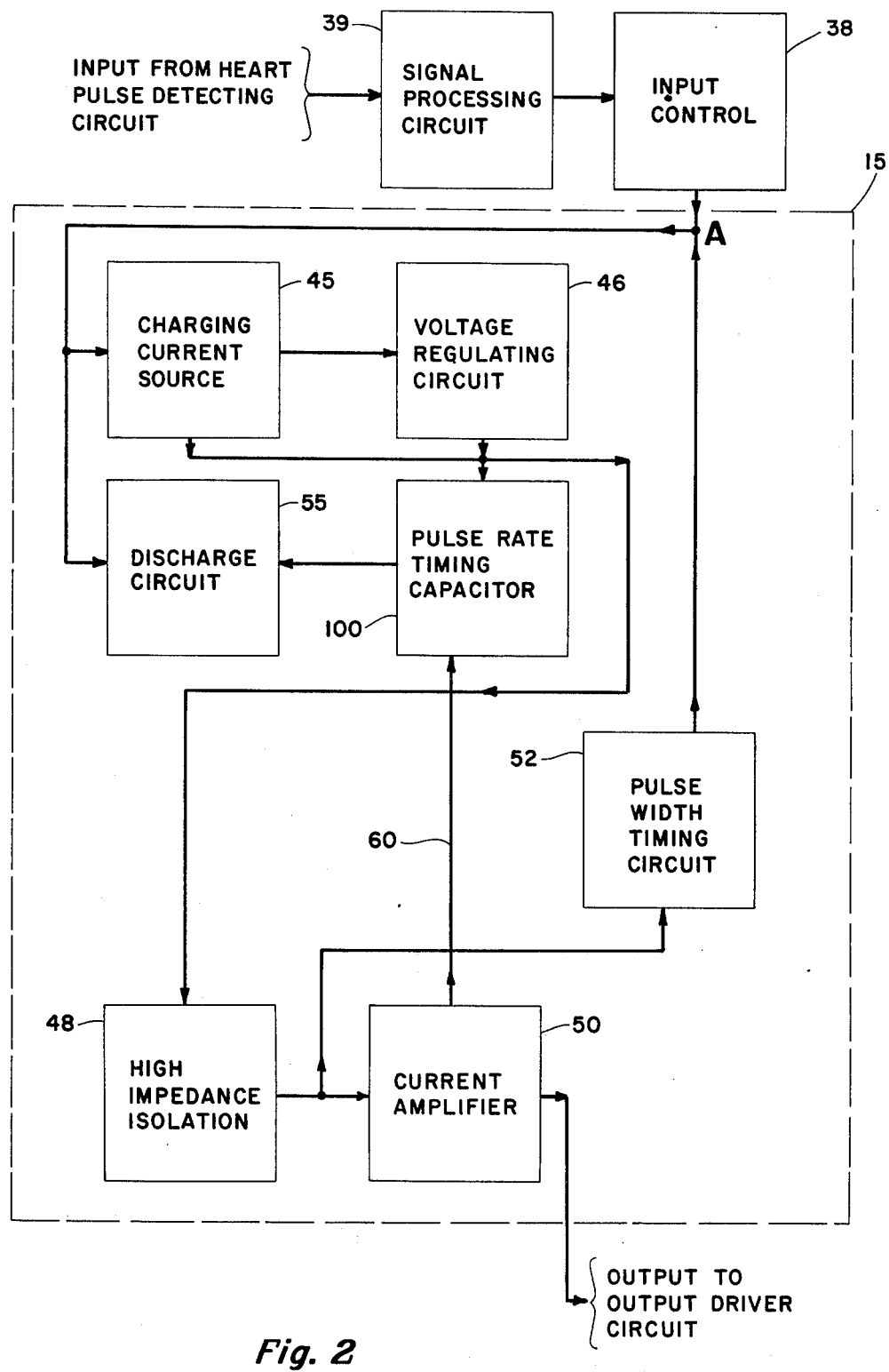
FIG. 2 is a box diagram of the oscillator portion of the block diagram of FIG. 1.

The oscillator 15 is shown more particularly in FIG. 2, and includes an imput control 38 (presented within the oscillator inhibitor 25 in FIG. 1) to which the signal from a signal processing circuit 39 (presented within the amplifier stage 20, the refractory clamp 21 and one-shot multivibrator 24 in FIG. 1) is applied.

The frequency or pulse rate of the oscillator is controlled by a pulse rate timing capacitor 100 which is charged periodically by a charging current source 45 to a voltage controlled by a voltage regulating circuit 46. The pulse rate timing capacitor 100, in combination with the voltage regulating circuit 46 activates a high impedance isolation section 48 having an output which is applied to an output current amplifier 50. (In the embodiment illustrated, the output current amplifier 50 is used as an inverter, amplifier, and driver to the voltage multiplier output section 17, shown in FIG. 1). The high impedance isolation 48 additionally has its output conducted to a pulse width timing circuit 52, which is fed back through the input to the charging current source 45 and to a discharge circuit 55, also connected to the pulse rate timing capacitor 100.

In the overall operation of the oscillator 15, the pulse rate timing capacitor is charged by the charging current source 45 until it reaches a voltage which activates the high impedance isolation section 48, driven by the voltage regulating circuit 46. The isolation section transmits a pulse to the current amplifier 50, and concurrently, to the pulse width timing circuit 52. The current amplifier 50 produces an output for multiplication within the voltage multiplier output section 17 (see FIG. 1), and, the pulse width timing circuit 52 begins timing the pulse. After the pulse has existed for the predetermined time, determined by the pulse width timing circuit 52, the discharge circuit 55 is activated, discharging the remaining charge of the timing capacitor 100, and starting the cycle anew. Also, a feedback line 60 is provided between the current amplifier and the pulse rate timing capacitor for positive feedback to effect fast switching.

Figure 3:
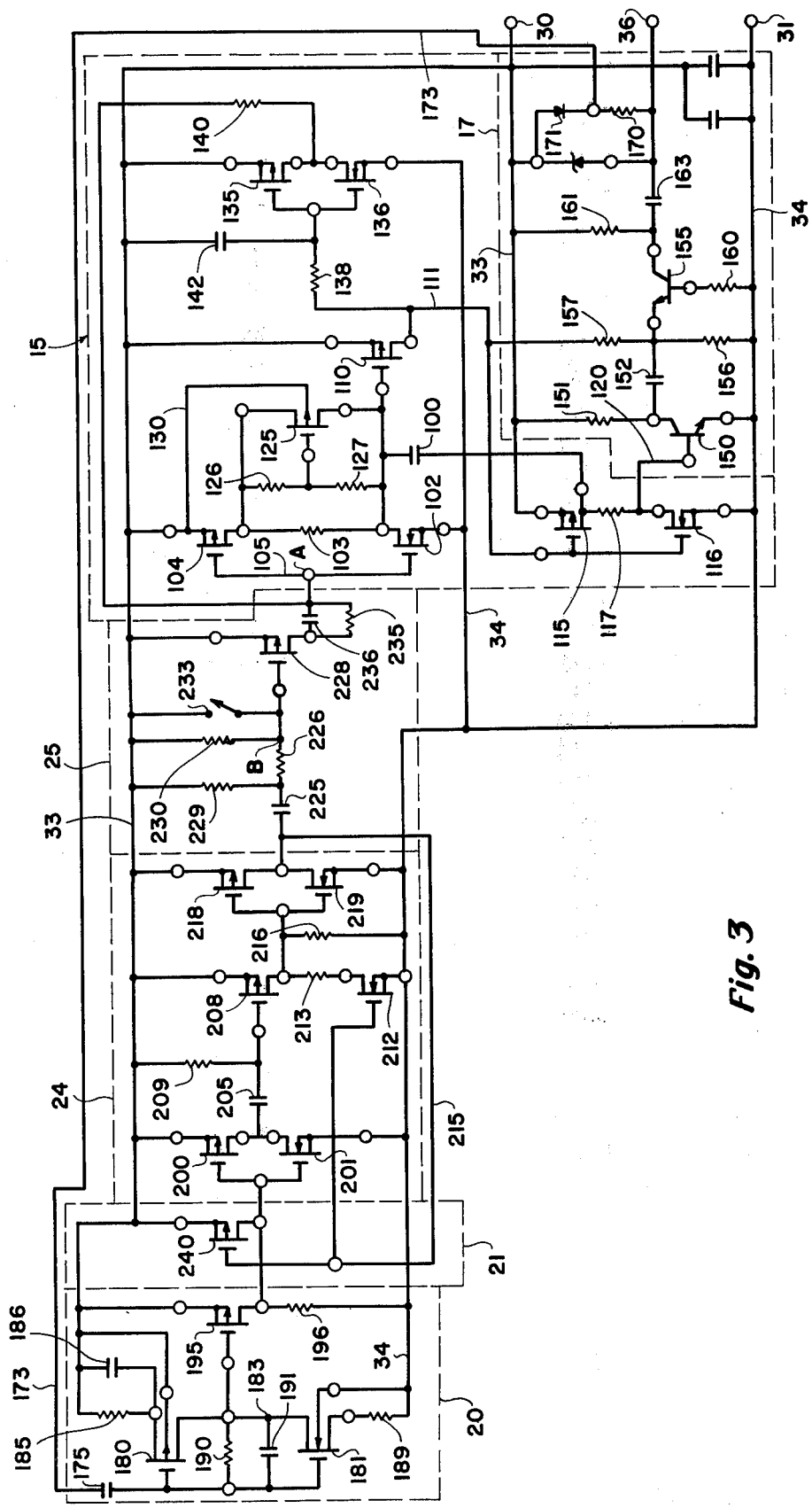
FIG. 3 is an electrical schematic diagram of a heart pacer, in accordance with the invention, corresponding to the box diagrams of FIGS. 1 and 2.

With reference now to FIG. 3, a schematic diagram of a heartpacer circuit, in accordance with the invention, the portions of the circuit above-described with reference to the box diagram of FIGS. 1 and 2 are indicated by dotted line portions. The power supply (not shown) is connected to the circuit at terminals 30 and 31 to define respectively a positive bus 33 and a negative bus 34. The heart lead is connected at terminal 36, the potentials thereon being referred to hereinafter as being with respect to the positive potential of the positive bus 33.

With reference now specifically to the oscillator section 15 of the schematic, the oscillator 15, produces pulses upon the charging and discharging of the timing capacitor 100. The timing capacitor 100 is connected at one side to the drain of the n-channel MOS device 102. The base and source elements of the MOS device 102 are connected to the negative bus 34, and the drain of the MOS device 102 is connected by a resistor 103 to the p-channel MOS device 104. The base and source elements of the MOS device 104 are connected to the positive bus 33, and the gates of CMOS devices 102 and 104 are connected together by line 105. It is to this gate interconnection line 105 that the pulse from the preceding sections, initiated by a naturally occurring heart pulse is applied, for example, at point A.

The drain of the MOS device 102, to which the capacitor 100 is attached at one side, is also attached to the gate of an FET device 110. The base and source of the FET 110 are connected to the positive bus 33, and the drain is connected to an oscillator output line 111.

The other side of the capacitor 100 is connected to the drain of MOS device 115, which is coupled to the drain of the complimentary MOS device 116 by resistor 117. The base and source of the MOS device 115 are connected to the positive bus 33, and, likewise, the base and source of the MOS device 116 are connected to the negative bus 34. The oscillator output line 111 is connected to both gates of the MOS devices 115 and 116. The output of the inverter-amplifier section, including MOS devices 115 and 116, is taken from the drain of the MOS device 116 upon line 120 for further amplification and application to the heart terminal 36 as below described.

To regulate the voltage charged upon the capacitor 100, a voltage regulator is provided, including an FET device 125. The gate of the FET device 125 is connected between two series connected resistors 126 and 127 which form a voltage divider for the voltage developed across a resistor 103, across which the resistors 126 and 127 are connected. Additionally, the source and drain of the FET device 125 are connected across the resistor 103, and the base is referenced to the positive bus 33 by connection line 130.

The width of the pulse generated is controlled by the circuit including CMOS devices 135 and 136. The gates of the respective CMOS devices 135 and 136 are connected to the output line 111 by a resistor 138 and the base and source of each of the CMOS devices 135 and 136 are connected, respectively, to the positive bus 33 and the negative bus 34. The drain elements are interconnected, and are fed back by a resistor 140 to the input point A upon the gates of the CMOS devices 102 and 104. A capacitor 142 is connected from the gates of CMOS devices 135 and 136 to the positive bus 33, and, in combination with resistor 138, functions to control, in part, the width of the pulse generated by the oscillator.

In operation of the oscillator and immediately associated circuits, the capacitor 100 is charged from the positive bus 33 through the source and drain of the MOS device 104, and the resistor 103, on one side, and through the resistor 117, and the drain and source of the MOS device 116 on the other side. In the embodiment illustrated, the MOS devices 104 and 116 are biased to normally on or conducting states.

As the positive charge is built up upon the capacitor 100, it is conducted to the gate of the MOS device 110. As the voltage increases, the gate-to-source voltage difference decreases, turning off the normally conducting MOS device 110. The output line 111 connected to the source of MOS device 110 therefore becomes negative, turning on the normally non-conducting MOS device 115 and turning off the normally conducting device 116, to thereby produce an output pulse upon line 120 for amplification and application to the heart. Concurrently, the negative potential on the output line 111 is applied to the capacitor 142 through the resistor 138 to thereby negatively charge the capacitor 142. As the charge upon capacitor 142 is discharged by the resistor 138, the interconnected gates of CMOS devices 135 and 136 become more negative, thereby biasing the normally off MOS device 135 into conduction and biasing the normally of MOS device 136 to a non-conducting state. The output, therefore, upon the drains of the CMOS devices 135 and 136 becomes positive, the positive potential being conducted by the resistor 140 to the point A of the gates of the CMOS devices 102 and 104. The positive potential biases the CMOS device 102 into a conducting state and the CMOS device 104 into a non-conducting state. The charge upon the capacitor 100 is therefore discharged through the drain and source of the CMOS device 102 to the negative bus 34, and, when the charge upon the capacitor 100 becomes below the threshold voltage of the FET device 110, it again begins to conduct, raising the voltage on the output line 111 to that of the positive bus 33. Thus, the width of the negative pulse exhibited upon the output line 111 is controlled by the charging rate of the capacitor 142 determining the time at which the respective CMOS devices 135 and 136 are caused to respectively conduct and non-conduct, and the time of discharge of the capacitor 100 after the positive pulse from the drains of the CMOS devices 135 and 136 are applied to the input point A of the CMOS devices 102 and 104.

The voltage charged upon the capacitor 100, as above mentioned, is regulated by the voltage regulator including the FET device 125. This is achieved by the voltage divider network including resistors 126 and 127 across which the voltage of load resistor 103 is applied. Thus, any change in voltage upon the load resistor 103 changes the bias condition of the FET 125, thereby increasing or decreasing the output at the drain thereof to rapidly change the capacitor 100 to within a constant voltage from which it is slowly charged for the remainder of the cycle.

The output developed upon the output line 120 of the CMOS devices 115 and 116 is applied to the voltage multiplication circuit, including an NPN transistor 150. The emitter of the NPN transistor 150 is connected to the negative bus 34 and the collector is connected by a resistor 151 to the positive bus 33. A capacitor 152 is connected between the collector of the NPN transistor 150 and the emitter of a second NPN transistor 155. Additionally, the emitter of the transistor 155 is connected by resistor 156 to the negative bus 34, and is also connected by a resistor 157 to the output line 111 from the oscillator. The base of the transistor 155 is connected by a resistor 160 to the negative bus 34, and the collector of the transistor 155 is connected by a resistor 161 to the positive bus 33. A second capacitor 163 is connected in series with the collector of the transistor 155 and the output terminal 36.

In operation of the voltage multiplier section 17, between pulses, charges are built up upon capacitors 152 and 153 from the positive and negative buses 33 and 34. Upon application of the pulse to the base of the transistor 150, the transistor 150 begins to conduct, causing the transistor 155 also to conduct. The charge upon the capacitor 152 and the voltage developed across the load resistor 151 are therefore combined, to thereby present an output voltage of increased potential from that originally presented.

The resistor 157, between the emitter of the transistor 155 and the output line 111 serves as a load upon the drain of the FET 110, and also serves to provide DC bias thereto. Additionally, when the transistor 155 conducts, the resistor 157 feeds back a negative potential to the oscillator circuit and pulse width determining circuit, thereby to aid in turning off the pulse generated thereby.

Although not shown, to further assist in supply voltage regulation, the source and drain of an FET, its base referenced to the negative bus 34, can be connected in series with the resistor 157 thus varying its value. By interconnecting the gates of such FET and the FET device 110, to form a CMOS pair, and by referencing the end of the resistor 138 away from the capacitor 142 to the collector of transistor 150, such positive feedback to the oscillator can be also achieved.

The circuit thus described constitutes the basic fixed rate heartpacer circuit which generates pulses at the rate and the width controlled by the oscillator, amplified by the amplifier and voltage multiplication stage including transistors 150 and 155 to be applied to the heart lead terminal 36.

To effect a demand capability of the circuit, the naturally occurring heart pulses are conducted through the heart lead (not shown) to the heart terminal 36, and referenced through a resistor 170 in series with a diode 171, to the positive bus 33. The diode 171 serves to clamp the output pulse to a predetermined voltage level to prevent overload or saturation of the amplifier stages, below described. The potential of the naturally occurring heart pulse is conducted from the interconnected diode 171 and resistor 170 via line 173 to the amplifier stage 20 through series capacitor 175. The line 173 through capacitor 175 is therefore connected to the gates of the CMOS devices 180 and 181. The drains of the CMOS devices 180 and 181 are interconnected by a line 183. The source of the MOS device 180 is connected by a resistor 185 in parallel with a capacitor 186 to the positive bus 33. In a similar manner, the source of the MOS device 181 is connected by a resistor 189 to the negative bus 34. The base of the CMOS device 180 is referenced by connection to the positive bus 33, and, the base of the MOS device 181 is referenced by connection to the negative bus 34. Additionally, the gates and drains of the CMOS devices 180 and 181 are interconnected by a resistor 190 in parallel with a capacitor 191. The drains of the CMOS devices 180 and 181 are also connected to the gate of an FET 195 for further amplification. The base and source of the FET 195 are connected to the positive bus 33 and the drain of the MOS device 195 is connected by a resistor 196 to the negative bus 34.

In operation, the CMOS devices 180 and 181, and the FET 195 are biased into normally conducting states. The pulse from the heart led 173, low frequency filtered by the resistor 170 and the capacitor 175, is applied to the gates of the CMOS devices 180 and 181. The pulse, high frequency filtered in amplification by the CMOS devices 180 and 181 by the parallel combination of the resistor 190 and the capacitor 191 is then applied to the gate of the FET 196 for further amplification. The output of the FET 195 is developed across the load resistor 196, and is inverted in polarity by a CMOS inverter circuit, including CMOS devices 200 and 201.

The first stage of the amplifier can alternatively be fabricated, if desired, by deleting the resistor 185 and capacitor 186 and replacing them with a direct connection between the source of the CMOS device 180 and the positive bus 33. If this is done, a resistor (not shown) can be employed to replace the connection between the drains of the CMOS devices 180 and 181, and the output derived from the drain of the CMOS device 181 instead of the drain of the CMOS device 180, to the gate of the FET 195.

The CMOS devices 200 and 201 of the inverter circuit have their gates interconnected and their drains interconnected. The base and source of the MOS device 200 are connected to the positive bus 33, and, likewise, the source and base of MOS device 201 are connected to the negative bus 33. The signal from the final amplifier FET 195, therefore is applied to the gates of the inverter CMOS devices 200 and 201, and the inverter output is derived from the drains of the CMOS devices 200 and 201.

The output from the inverter is applied through a capacitor 205 to the gate of an MOS device 208 of the monostable or one-shot multivibrator section 24. The gate of the MOS device 208 is connected by a resistor 209 to the positive bus 33. Thus, the pulse shape applied to the gate of the MOS device 208 represents a short positive pulse followed by an integrated negative pulse produced by the combined effect of the discharging capacitor 25 and the resistor 209. The source and base of the MOS device 208 are connected to the positive bus 33, and the drain is connected to the drain of the complimentary MOS device 212 by resistor 213. The complimentary MOS device 212 has its source and base connected to the negative bus 34 and its gate connected to the output of the one-shot multivibrator by line 215. The drain of the MOS device 208 is connected by a resistor 216 to the negative bus 34, and the two gates of the CMOS devices 218 and 219. The gates of the MOS devices 218 and 219 are interconnected, as are the drains, again to form a pulse inverter circuit. The source and base of the MOS device 218 are connected to the positive bus 33, and the source and base of MOS device 219 are connected to the negative bus 34.

In operation, a pulse from the inverter CMOS devices 200 and 201 is applied to the capacitor 205. As the signal is integrated by the capacitor 205, the MOS device 208 is forward biased upon presentation of the negative signal portion. The forward biasing of the MOS device 208 produces an output across the resistor 216, causing the normally non-conducting MOS device 219 to be switched into conduction. The output at the drains of the CMOS devices 218 and 219 thereupon becomes negative, which, when applied to the gate of the MOS device 201, changes the state from normally on to a non-conducting state. Upon this change of state of the MOS device 212, the voltage developed across the resistor 213 becomes more positive at its connection with the drain of the CMOS device 208, thereby tending to switch the CMOS device 218 further off and the CMOS 219 further on. As the negative charge capacitor 205 becomes discharged by the resistor 209, the gate of the MOS device 208 becomes more positive, thereby turning the MOS device 208 back into non-conduction. There-upon, the drain of the MOS device 208 becomes negative, biasing the CMOS device 218 on and the CMOS device 219 off. The drains of the CMOS devices 218 and 219, therefore, become positive, the positive potential being fed back to the gate of the MOS device 212, to thereby bias the MOS device 212 on to cause the drain of the CMOS device 208 to become more negative, thereby further turning the CMOS device 218 on and the CMOS 219 off.

The output pulse from the one-shot or monostable multivibrator section 24 is applied to a capacitor 225 connected in series with a resistor 226 to the gate of an FET 228. A resistor 229 interconnects the junction between the resistor 226 and the gate of the FET 228 to the positive bus 33. A switch, such as a reed switch or magnetically activated switch 233 is connected across the resistor 230, between the gate of the FET 228 and the positive bus 33. The base and source of the FET 228 are connected to the positive bus 33, and the drain of FET 228 is connected by a parallel connected resistor 235 and capacitor 236 to the point A or the input of the oscillator section 15.

To present a capability for the circuit to define a refractory period or a period during which additional incoming signals are not detected, an FET 240 is provided. The base and source of the FET 240 are connected to the positive bus 33 and the drain is connected to the gate of the CMOS devices 200 and 201. The gate is connected by a line 215 to the output at the drains of the CMOS devices 218 and 219 of the one-shot multivibrator. Thus, when a negative potential is exhibited at the output of the one-shot or monostable multivibrator upon the drains of the CMOS devices 218 and 219, it is conducted by line 215 to the gate of the FET 240 to bias it on, thereby placing the gates of the CMOS devices 200 and 201 at a positive potential to bias the CMOS device 200 off, and bias the CMOS device 201 on. For the period of the duration of the negative output of the one-shot multivibrator, any additional incoming signal detected and amplified by the amplifier section 20 will not be received in the inverter and one-shot or monostable multivibrator sections, and, thereore, will be ineffective in resetting the timing period of the oscillator.

In operation, a detected pulse from the one-shot multivibrator section 24 will be applied through the oscillator inhibitor section 25 to point A. If this occurs, point A will be driven to a positive potential, thereby activating the CMOS device 102 (turning it to a conducting or on state) and turning off CMOS device 104, thereby stopping the charging of the capacitor 100, through the CMOS device 104 and causing the discharging of the capacitor 100 through the CMOS device 102. Upon reception of the heart signal by the amplifiers, monostable multivibrator, and oscillator inhibitor, the charge upon capacitor 100 is discharged or dumped and the charging process begun anew.

Figure 4:
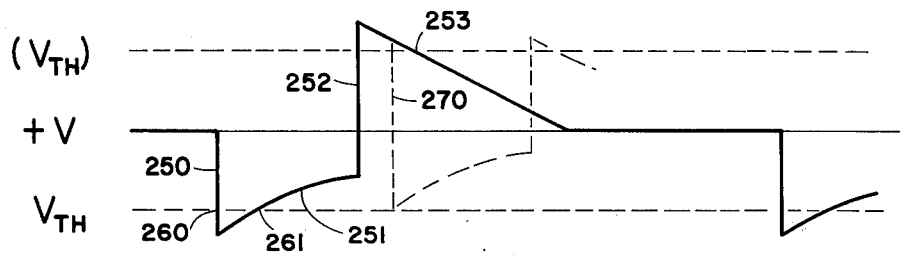
FIGS. 4, 5, and 6, are voltage wave forms taken at point A in FIG. 3, representing voltage verses time for normal, reduced voltage and extraneous noise operating conditions, respectively.
Figure 5:
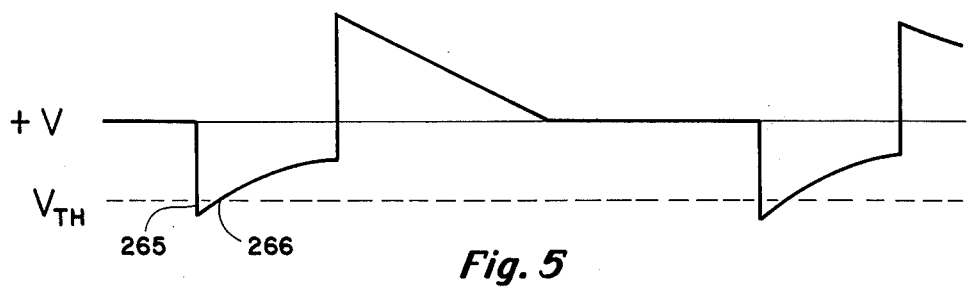
Figure 6:
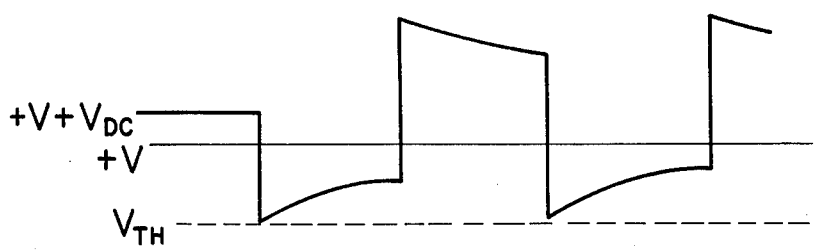

More particularly, with respect to the operation of the oscillator inhibitor section 25 with reference to FIGS. 4-6, which reflect the voltage waveforms observed at point B in the oscillator inhibitor section shown in FIG. 3, it can be seen that a negative square wave pulse produced on the drains of the CMOS devices 218 and 219 produces an initial downward impulse shape 250, from the initial voltage +V normally impressed at point B. As soon as the voltage exceeds the threshold voltage $V_{TH}$ (the threshold voltage of FET 228) the FET 228 will be biased into a conducting state. As the charge upon the capacitor 225 is discharged by the resistor 229 it will exhibit an exponential shape, as shown by the curve 251. Upon the application of the trailing edge of the square wave upon the drains of the CMOS devices 218 and 219, the waveform at point B will become immediately positive, as illustrated wave-form portin 252. The positive voltage at point B will thereafter decay, as shown by curve 253, and the cycle repeated after the normal heartbeat period.

It can be seen that the FET 228 will be biased into a conduction state during the portion of time in which the voltage at point B is below the threshold voltage $V_{TH}$ shown in FIG. 4 by points 260 and 261. As the supply voltage decreases, such as by old age or normal deterioration of the battery, or other like cause, the amplitude of the voltage of the waveform at point B will also decrease in a manner relatable to the change of magnitude of the supply voltage. Thus, as shown in FIG. 5, the portion of the waveform which pierces the $V_{TH}$ level, between, for example, points 265 and 266 is smaller than that produced by the larger amplitude waveform of FIG. 4 between points 260 and 261. Since the time period which the FET 228 is in a conduction state determines the time which the CMOS device 102 wll also be in a conduction state to discharge the capacitor 100, it can be seen that as the supply voltage decreases, the time of conduction of the MOS device 228 will decrease, and the capacitor 100 will be held in discharge less time per pulse period. This will result in an increase in the frequency of the oscillator, since the capacitor 100 will charge faster to the threshold voltage of the FET 110. It can be seen that this frequency increase is of advantage in determining the state or condition of the power supply to which the circuit is attached, especially after prolonged periods of use, for instance, over many years, when the state of deterioration of the power supply or battery becomes questionable.

Furthermore, by the inclusion of the switch 233, which can be activated by placing a magnet in proximity thereto, the circuit can be placed into a fixed rate configuration or mode in which the pulses detected and amplified from the preceding sections are bypassed and are of no effect on the timing of the oscillator circuit. This presents additional advantages in the particular circuit configuration shown. For example, since the device is intended for long-term use, primarily in conjunction with a long life nuclear battery or the like, variations in component values may occur which affect or vary the oscillation frequency. Nevertheless, such variations will affect the frequency both in the fixed rate mode with the reed switch closed, and in the demand or inhibit mode with the reed switch 233 open.

Thus, over a long period of time, the condition of the battery can nevertheless be ascertained or determined by comparing the charge in the difference of the oscillator frequency in the fixed rate mode and in the demand mode. That is, the change due to component value drifts, and other causes, will have the same effect upon the oscillator frequency in both the fixed rate and demand modes. However, the amplitude of the supply voltage will affect the frequency of the oscillator primarily in the demand mode by virtue of the change in amount of waveform beneath the threshold voltage, described above with reference to FIGS. 4 and 5. Consequently, regardless of the life of the circuit, the difference between the rate of oscillator frequency in the fixed rate mode and in the demand mode will indicate the state or condition of the battery or power source.

The circuitry of the oscillator inhibitor 25 has an additional advantage in extending the refractory period of the circuit. For example, the refractory period as explained above is primarily defined by the explained, during of the pulse of the one-shot multivibrator section 24. As explained, during the length of the output pulse from the multivibrator, the FET 240 is maintained in conduction, thereby shorting the gate of the CMOS devices 200 ane 201 to the positive bus 33. This, typically, defines a refractory period on the order of 125 milli-seconds.

It can be seen from FIG. 4 that in the wave form produced by the capacitor 225, the duration of the pulse defined by lines 250, 251, and 252 is the length of the output pulse from the one-shot multivibrator stage 24, or approximately 125 milli-seconds. If, for example, another pulse is detected and and amplified immediately after the expiration of the 125 milli-seconds period of the refractory period, defined by the clamp of FET 240, as shown by the dotted line in FIG. 4, and if such pulse occurs within the portion of the curve prior to the point 253, corresponding to a threshold voltage of opposite polarity from the +V line, (shown by the dotted line ($V_{TH}$) ) the waveform 270 will not reach the $V_{Th}$ required to cause MOS device 228 to conduct. This defines an effective additional time period during which detected pulses are not permitted to inhibit the charging of the oscillator timing capacitor 100.

The oscillator inhibitor 25 additionally functions to reject high frequency noise; that is, to cause the oscillator to function at a fixed rate rather than syncing to an undesirable frequency detected and permitted to pass. This is important, for example, if the wearer or user of a heartpacer is in an environment of noise, for example, from a microwave oven, automobile ignition systems, or the like. The charge applied to the capacitor 225, if the frequency is sufficiently high, will not be bled off or discharged by the resistor 229 within the usual heartbeat frequency time, and, as shown in FIG. 6, a DC bias will be observed at point B impressed upon the waveform produced. If the DC bias equals the normal voltage +V, plus an amount equal to the threshold voltage $V_{TH}$ to turn on the FET 228, since the FET 228 remains non-conducting, the oscillator 15 will produce pulses at the fixed rate.

Another of the particular advantage of the oscillator inhibitor circuit 25 in combination with the oscillator 15, as illustrated, is that it automatically rejects noise or other extraneous signals detected by the circuit which are at a frequency of approximately twice that of a normal heartbeat. This is achieved by effecting a reduction of the refractory period upon reception of noise greater than a frequency of twice that of an acceptable heart rate. This is of importance since if noise at such heart rate multiple frequency is received, the circuit will automatically block one of the noise cycles by virtue of the predefined refractory period block or clamp. Thus, the circuit could act as a frequency divider, detecting a pulse rate of half that which is in reality being received. The circuit, therefore, could be tricked, absent the ability to present a reduced refractory period, into syncing onto every other pulse of the higher frequency noise.

For example, if an acceptable heartbeat rate is 125 ppm (pulses per minute) having a period of 480 ms, and noise is received having a period of 240 ms (corresponding to an unacceptable heartbeat rate of 250.00 ppm), the noise will be divided by 2 (every other pulse falling within a 250 ms refractory clamp) thus being detected as an acceptable heartbeat rate of 125 ppm, and undesireably inhibiting stimulation pulse production.

However, since the refractory period in the circuit described with reference to FIG. 3 defines its refractory period by the sum of the time of the clamp provided by the FET 240 (a fixed time depending on the time constant of the capacitor 205 and the resistor 209) and the time of the reverse bias on the FET 228 provided by the capacitor 225 and the resistor elements 229, 226, and 230 (a variable time depending upon the frequency of the pulses received as above described), the effective refractory period will be reduced, thereby detecting all the higher frequency pulses as not blocked by the clamp heartbeats and the oscillator will be switched to a fixed rate mode by the high frequency rejection feature.

The circuit above described can be fabricated by any well known technique. Because of the ultimate intended use, however, of being implanted within a human, size is a relevant consideration in the circuit design. Conveniently, the circuit can be formed with discrete parts or elements upon a printed circuit board, or, alternatively, can be fabricated in its entirety, except for the CMOS and FET devices upon a single substrate by known thick film or thin film techniques wherein the capacitors and resistors, for instance, are etched or otherwise formed from the material of the substrate, to achieve a particularly small sized circuit.

In the embodiment shown, the various components can be of the following illustrative values:

| Resistors | |
|---|---|
| 103 | 12 M ohms |
| 117 | 6.8 K " |
| 126 | 4.4 M " |
| 127 | 7.2 M " |
| 138 | 6.5 M " |
| 140 | 1.2 M " |
| 151, 156 | 4.7 K " |
| 157 | 750 K " |
| 160, 161 | 15 K " |
| 170 | 10 K " |
| 185 | 55 K " |
| 189 | 510 K " |
| 190 | 20 M " |
| 196, 216, 235 | 4.3 M " |
| 209 | 1.5 M " |
| 213 | 27 K " |
| 226 | 13 M " |
| 229 | 2.2 M " |
| 230 | 6 M " |

| Capacitors | |
|---|---|
| 100 | 0.15 microfarad |
| 142 | 270 picofarad |
| 152, 163 | 22 microfarad |

-continued

| | |
|---|---|
| 175, 205, 236 | 0.047 " |
| 186 | 0.47 microfarad |
| 191 | 50 picofarad |
| 225 | 0.1 microfarad |
| Transistors | |
| 180, 181, 195, 200, 201 | TA6178 |
| 208, 212, 218, 219, 240 | " |
| 115, 116, 135, 136, 228 | " |
| 102, 104, 110, 125 | " |
| 150, 155 | 2N2222A |

In the fabrication of the circuit, the use of FEt devices, as above described can be achieved by employing one of a pair of CMOS transistors, for example, without making connection to its complement. This would be feasible, for instance, if a number of CMOS pairs are used within a single integrated circuit package, as are now widely commercially available.

Although the invention has been described and illustrated with a certain degree of particularity, it is understood that the present disclosure is made by way of example only and that numerous changes in the combination and arrangement of course may be resorted to by those skilled in the art without departing from the spirit and scope of the invention as hereinafter claimed.

What is claimed is:

1. An oscillator comprising:
    a pair of complementary metal oxide semiconductors, each having a source, a gate, and a drain,
    said gates being interconnected, and the respective sources of which being connectable to terminals of opposite polarity of a source of electric potential,
    a resistor interconnected between the drains of said complementary metal oxide semiconductors,
    a capacitor connected at one side to the drain of one said complementary metal oxide semiconductors,
    means connecting said capacitor at its other side to said source of said complementary metal oxide semiconductor to the drain of which said one side of said capacitor is connected,
    a field effect transistor, having a source, a gate, and a drain,
    said gate being connected to the drain of said complementary metal oxide semiconductor to which said one side of said capacitor is connected,
    said source being connected to one of said terminals of said source of electrical potential,
    a resistor connected between the drain of said field effect transistor and the other of said sources of electric potential, and
    timing means for providing a bias to the gates of said complementary metal oxide semiconductors normally biasing said complementary metal oxide semiconductor to which said capacitor is connected to non-conducting state, and to bias the other of said complementary metal oxide semiconductors to a conducting state, whereby when said capacitor charges to the threshold voltage of said field effect transistor, said field effect transistor is biased into a non-conducting state, thereby initiating said timing means to apply a bias voltage of opposite polarity from said normal biasing to bias said complementary metal oxide semiconductor to which said capacitor is connected to a conducting state, and the other complementary metal oxide semiconductor to a non-conducting state, thereby discharging said capacitor.

2. The oscillator of claim 1 further comprising oscillator disabling means including:
    a pair of complementary metal oxide semiconductors each having a gate, a drain, and a source,
    said gates being interconnected, said drains being interconnected, and said sources each being connected to a respective one of said terminals of said source of electric potential,
    a resistor and a capacitor, connected in series between the drain of said field effect transistor and one of said terminals of the source of electric potential, the interconnection between said capacitor and resistor being connected to said gates of said pair of complementary metal oxide semiconductors last above mentioned, and
    means for connecting the drains of said last mentioned complementary metal oxide semiconductors to said gates of said complementary metal oxide semiconductors of said oscillator,
    whereby when an output pulse is produced by said field effect transistor, said series connected capacitor and resistor change after a predetermined delay the conduction states of said last mentioned pair of complementary metal oxide semiconductors to cause said complementary metal oxide semiconductors of said oscillator to change conduction states, thereby discharging said timing capacitor.

3. The oscillator of claim 2 further comprising a voltage regulator connected to said capacitor of said oscillator to regulate the voltage charged thereupon.

4. The oscillator of claim 3 wherein said voltage regulator comprises:
    a pair of resistors connected in series, said series connected in parallel with said resistor interconnected between the drains of said complementary metal oxide semiconductors of said oscillator to form a voltage divider,
    a field effect transistor having a base, a source, a gate, and a drain, said base being connected to one of said terminals of said potential source, said gate being connected to the junction between said voltage divider resistors, said source being connected to the drain of one said complementary metal oxide semiconductors of said oscillator, and said source being connected to the drain of the other of said complementary metal oxide semiconductors of said oscillator.

5. The oscillator of claim 4 further comprising waveform generating means for changing the conduction states of said complementary metal oxide semiconductors of said oscillator.

6. The oscillator of claim 5 wherein said waveform generating means comprises:
    a field effect transistor having a source, a gate, and a drain, said source being connected to one of said terminals of said electric potential,
    means for generating a square wave,
    a capacitor to which the generated square wave is applied, connected in series with the gate of said field effect transistor,
    a resistor connected between the terminal of said capacitor away from said side to which the square wave is applied and the source of said field effect transistor,
    a second capacitor, and a second resistor said second capacitor and second resistor being connected in parallel, and interconnecting the drain of said field effect transistor and the gates of said complementary metal oxide semiconductors of said oscillator,
    whereby when the generated square wave is applied to said capacitor, said first mentioned capacitor and resistor differentiates at least a portion of the square wave, thereby producing a waveform having a portion extending below the threshold voltage of said field effect transistor.

* * * * *